United States Patent [19]

Tournier

[11] 4,384,472
[45] May 24, 1983

[54] APPARATUS FOR MEASURING VISCOSITIES AND DENSITY OF FLUIDS

[75] Inventor: Michel Tournier, Mont Saint Aignan, France

[73] Assignee: Exxon Research and Engineering Co., Florham Park, NJ

[21] Appl. No.: 242,425

[22] Filed: Mar. 11, 1981

[30] Foreign Application Priority Data

Mar. 13, 1980 [FR] France .................................. 8005653

[51] Int. Cl.³ .......................... G01N 9/32; G01N 11/02
[52] U.S. Cl. ............................................ 73/30; 73/32; 73/55
[58] Field of Search ................... 73/55, 23, 30, 861.59, 73/32 R

[56] References Cited

U.S. PATENT DOCUMENTS

| | | | |
|---|---|---|---|
| 2,728,219 | 12/1955 | Martin | 73/23 X |
| 2,934,944 | 5/1960 | Eolkin | 73/55 |
| 3,086,386 | 4/1963 | Kapff | 73/3 |
| 3,662,599 | 5/1972 | Masnik | 73/861.59 |

FOREIGN PATENT DOCUMENTS 923849 3/1947 France .

Primary Examiner—James J. Gill
Attorney, Agent, or Firm—Donald F. Wohlers

[57] ABSTRACT

An apparatus for measuring the viscosities and the density of fluids comprises:

(1) a first hydraulic bridge (I) having two diametrically opposed elements (2,3) through which fluid undergoes laminar flow and two diametrically opposed elements (4,5) through which fluid undergoes turbulent flow and means (6) connected to a junction (6) between one laminar element (2) and one turbulent element (5) and a junction (d) between the other turbulent element (4) and the other laminar element (13) capable of detecting the equilibrium of the bridge, (2) a first pump (1) controlled by the detecting means (b) and connected to the supply of fluid from which the fluid is fed into the first bridge (I), (3) a second hydraulic bridge (II) through which the fluid from the first bridge (I) can flow, said second bridge having four identical elements (9,10,11,12) through which the fluid from the first bridge (I) flows turbulently and a constant flow volumetric pump (13) connected to a point (B) between one pair of adjacent elements (9,12) and a point (D) between the other pair of adjacent elements (10,11), (4) means (8) for measuring the pressure drop across the first hydraulic bridge (I) and (5) means (14) for measuring the pressure drop across the second bridge (II).

6 Claims, 2 Drawing Figures

APPARATUS FOR MEASURING VISCOSITIES AND DENSITY OF FLUIDS

This invention relates to apparatus for measuring viscosities and density of fluids.

It is known to use a hydraulic bridge comprising two elements giving a laminar flow and two elements giving a turbulent flow. When such a bridge is kept balanced by controlling the fluid flow passing through it, simple relationships make it possible to derive measurements of viscosities of the fluid as a function of apparatus constants, pressure drop and volumetric flow across the bridge. The main difficulty is to make a precise enough measurement of the flow crossing the bridge when the characteristics of the fluid are variable.

We have found that by associating such a bridge with a second totally turbulent hydraulic bridge it is possible to make precise and reliable measurements to enable the viscosities and density of a fluid to be determined.

According to this invention, an apparatus for measuring viscosities of a fluid comprises (1) a first pump connected to the supply of fluid, (2) a first hydraulic bridge through which the fluid from the first pump can flow, said hydraulic bridge having two diametrically opposed elements through which the fluid undergoes laminar flow and two diametrically opposed elements through which the fluid undergoes turbulent flow and means capable of comparing the pressure at the two points situated between one laminar and one turbulent element, said means controlling the first pump so as to maintain equilibrium by varying the flow of fluid entering said first hydraulic bridge, (3) a second hydraulic bridge through which the fluid from the first bridge can flow, said second bridge having four identical elements through which the fluid can undergo turbulent flow and a second pump connected to a point between one pair of adjacent elements and a point between the other pair of adjacent elements, (4) means for measuring the pressure difference across the first hydraulic bridge and (5) means for measuring the pressure difference across the second bridge.

As will be explained later, it is possible by measuring the pressure differences across the two bridges to calculate the density, the dynamic viscosity and the kinematic viscosity of the fluid flowing across the apparatus.

The first pump may be of the variable flow type in which case it must be controlled by a pressure sensor to ensure equilibrium of the first hydraulic bridge. This first pump may be a constant flow volumetric pump in which case it is to be connected to a variable valve controlled by a pressure sensor in such a way that a flow corresponding to the equilibrium of this bridge is maintained in the first bridge.

In the first hydraulic bridge, the elements for laminar flow may be either a simple or multiple tube arrangement to get a sufficient pressure drop for a Reynolds number low enough to ensure true laminar flow, or some kind of porous material giving a pressure drop proportional to the flow of fluid crossing it. Those elements for turbulent flow may be simple jets giving a Reynolds number of the flow high enough to ensure true turbulent flow. It is essential that the turbulent elements be diametrically opposed and that laminar elements be diametrically opposed.

The bridge must be balanced automatically by adjusting the flow of fluid, that is to say the pressure drop across any laminar element must be equal to the pressure drop across any turbulent element. There is a device for comparing pressure at the opposite point of the bridge and this may be a null differential pressure detector.

The fluid leaving the first hydraulic bridge enters the second hydraulic bridge. This second bridge has four identical elements, one in each arm of the bridge, through which the fluid can flow turbulently. In this second hydraulic bridge, there is a pump giving a transverse fluid flow across the bridge. This pump must be a constant flow volumetric pump.

Finally, there are means for measuring the pressure differences across the first hydraulic bridge and means for measuring the pressure differences across the second hydraulic bridge. Means for making these measurements are for example differential pressure transducers of any type, accurate enough, and commercially available.

In a preferred but not exclusive embodiment, the two pumps are constant flow volumetric pumps and are driven by a common constant speed electric motor. In this case, the total flow of fluid through the first bridge and into the second hydraulic bridge is adjusted by a control valve governed by the null differential pressure detector of the first hydraulic bridge. This valve is conveniently situated in a by-pass line connecting the inlet to the first bridge with the exit from the second bridge.

The apparatus of this invention can have various uses, for example in manufacturing a product corresponding to given specifications when various constituents have to be mixed; it can also, as an example, be used for adjusting the settings of a heat engine or a fuel burner to suit the variable characteristics of the fluids which it uses.

Two preferred forms of the apparatus are now described with reference to the drawings in which the apparatus is shown schematically.

Figure 1:
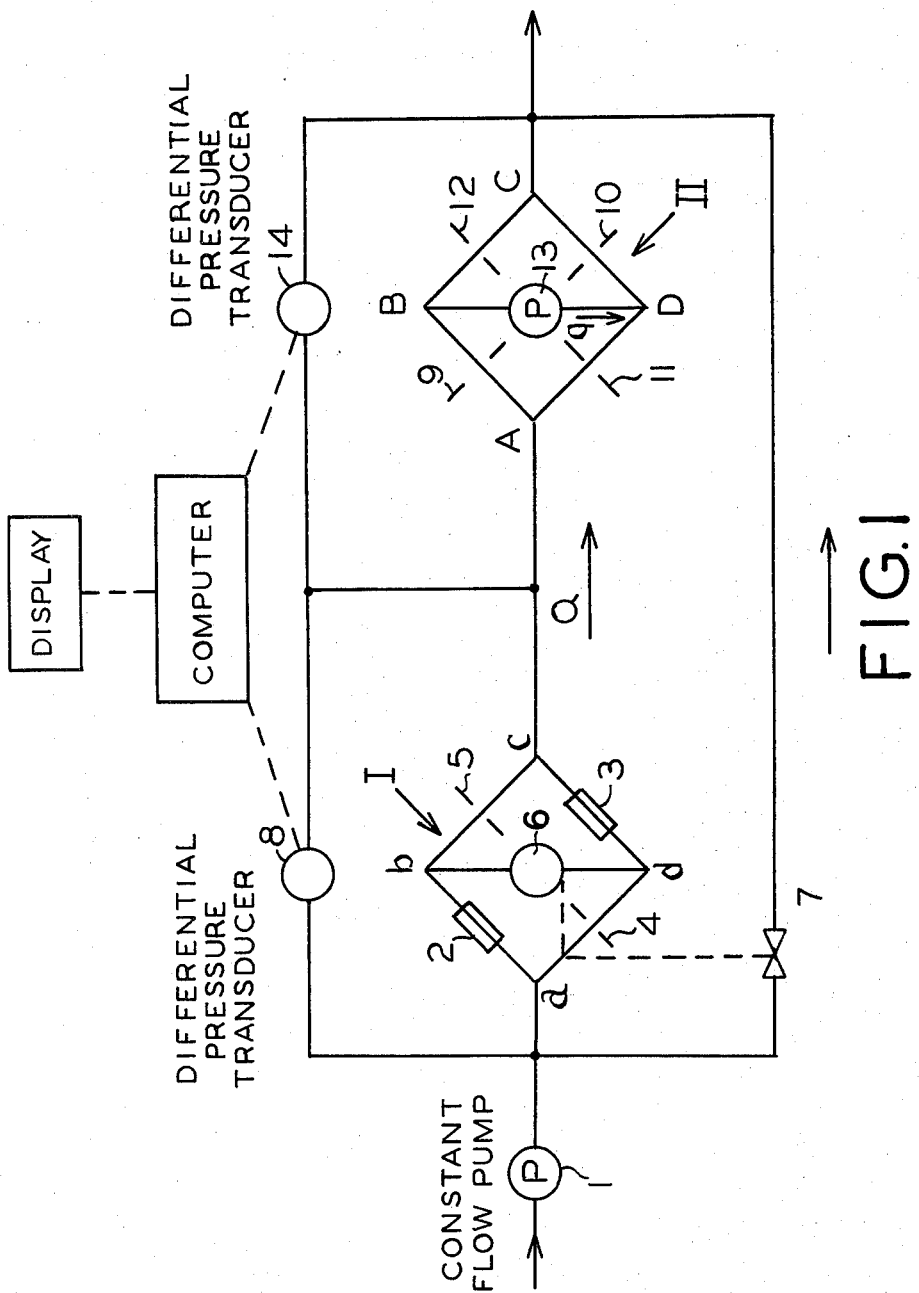
FIG. 1 shows a first embodiment wherein balanced flow in the first hydraulic bridge is obtained by bypassing a portion of the output of a constant flow pump through a bypass control valve.

Fluid from pump 1 enters the first hydraulic bridge I. This bridge comprises two elements 2 and 3 for laminar flow and two elements 4 and 5 for turbulent flow. The pressure difference between points b and d of this bridge I is measured by detector 6 and adjusted to zero by the control valve 7 to which this detector is electrically connected. The total pressure $\Delta P1$ across the first bridge I is determined by the differential pressure transducer 8.

In the second hydraulic bridge II, there are four identical elements 9-10-11-12 for turbulent flow and a constant flow volumetric pump 13. The total pressure difference $\Delta P2$ across the second hydraulic bridge is measured by the differential pressure transducer 14.

The first hydraulic bridge I must be balanced automatically by adjusting the flow of fluid through the apparatus. This is obtained by means of the control valve 7 which can be of the solenoid or motor-driven type governed by the detector 6. The operation of the FIG. 1 and FIG. 2 apparatus is as follows:

In the bridge I enters a volumetric flow Q coming from pump I. This flow is divided into two parts Q/2, equal if this bridge is at equilibrium. The pressure drop of laminar elements 2 and 3 is:

$$Pa - Pb = Pd - Pc = k_1 \eta Q/2 \quad \text{(dimension } ML^{-1}T^{-2}\text{)} \quad (1)$$

where Pa, Pb, Pc, and Pd are the pressures at junctions a, b, c and d, respectively and $K_1$ is an apparatus constant (having dimension $L^{-3}$), $\eta$ is the dynamic viscosity (dimension $ML^{-1}T^{-1}$), and Q the volumetric flow entering the bridge (dimension $L^3T^{-1}$).

The pressure drop of the turbulent elements 4 and 5 is:

$$Pa - Pd = Pb - Pc = k_2 d \left(\frac{Q}{2}\right)^2 \quad \text{(dimension } ML^{-1}T^{-2}\text{)} \quad (2)$$

where $k_2$ is another apparatus constant (dimension $L^{-4}$) and d is the density of the fluid (dimension $ML^{-3}$).

When this bridge I is balanced, that is Pb=Pd, by adjusting the flow Q passing through the bridge, then by subtracting the above two equations (1) and (2), we have:

$$k_1 \eta = k_2 d(Q/2) \quad (3)$$

or if $\nu$ is the kinematic viscosity (dimension $L^2T^{-1}$) then $$k_1 \nu = k_2(Q/2) \quad (4)$$

So, from addition of equations (1) and (2) we have $$\Delta P1 = Pa - Pc = \left(k_1 \eta + k_2 d \frac{Q}{2}\right) \frac{Q}{2}$$

or, from equation (3)

$$\Delta P1 = k_1 \eta Q = \tfrac{1}{2}(k_2 d Q^2) \quad (5)$$

In the bridge II, there are two flows:
(1) the flow Q is originating from bridge I, and
(2) the flow q which is constant and greater than Q, formed by the pump 13.

The fluid flow in the turbulent elements 9 and 10 is $(q/2)+(Q/2)$ and hence the pressure drop is:

$$P_A - P_B = P_D - P_C = k_4 d \left(\frac{q+Q}{2}\right)^2 \quad \text{(dimension } ML^{-1}T^{-1}\text{)} \quad (6)$$

where $P_A$, $P_B$, $P_C$ and $P_D$ are the pressures at junctions A, B, C and D, respectively and $k_4$ ($L^{-4}$) is another apparatus constant. Similarly, the flow in the elements 11 and 12 is $(q/2)-(Q/2)$ and hence the pressure drop is:

$$P_D - P_A = P_C - P_B = k_4 d \left(\frac{q-Q}{2}\right)^2 \quad (7)$$

By substracting equation (7) from equation (6), we have $$\Delta P_2 = P_A - P_C = k_4 d \left[\left(\frac{q+Q}{2}\right)^2 - \left(\frac{q-Q}{2}\right)^2\right] = \quad (8)$$

$$k_4 q Q = k_3 d Q$$

where $k_3 = q \cdot k_4$ is another constant (dimension $L^{-1}T^{-1}$) since q is kept constant. From equation (8) we have:

$$Q = \frac{\Delta P_2}{k_3 d} \quad (9)$$

This value with equations (3) and (4) gives:

$$\eta = \frac{k_2}{k_1} d \frac{Q}{2} = \frac{k_2}{2 k_1 k_3} \Delta P_2 \quad (10)$$

$$\nu = \frac{\eta}{d} = \frac{\Delta P_1}{k_1 dQ} = \frac{k_3}{k_1} \frac{\Delta P_1}{\Delta P_2} \quad (11)$$

$$d = 2\frac{\Delta P_1}{k_2 Q^2} = \frac{k_2}{2 k_3^2} \frac{(\Delta P_2)^2}{\Delta P_1} \quad (12)$$

If the constants k1, k2 and k3 are known from the apparatus construction and $\Delta P1$ and $\Delta P2$ are measured in the form of electrical signals, equations (10) (11) and (12) enable one to calculate the three variables $\eta, \nu$ and d by means of an analogous or numerical electronic network consisting of commercially available components as multipliers, dividers and displays or recorders.

Figure 2:
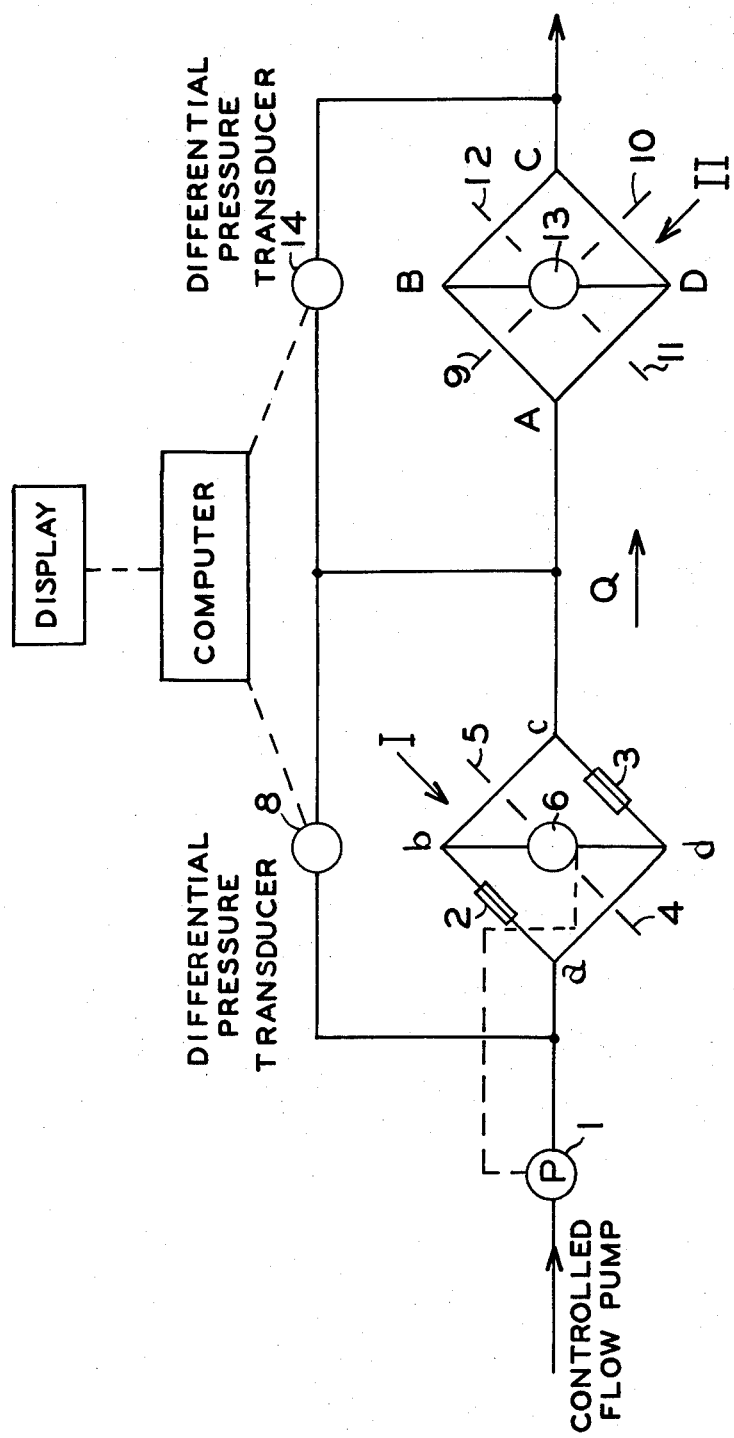
FIG. 2 shows a second embodiment of the invention wherein balanced flow in the first hydraulic bridge is obtained by controlling the flow of a variable flow pump.

In the embodiment of FIG. 2, similar reference materials have been applied as in FIG. 1 to designate similar elements having similar functions. In this embodiment however pump 1 is a variable flow pump and is controlled by the pressure detector 6 so as to vary the flow from the pump 1 to maintain a zero pressure differential between points b and d. In all other respects the arrangement of FIG. 2 operates in the same manner as that previously described for FIG. 1.

What is claimed is:
1. An apparatus for measuring the viscosities and the density of fluids which comprises:
(1) a first hydraulic bridge having two diametrically opposed elements through which fluid undergoes laminar flow and two diametrically opposed elements through which fluid undergoes turbulent flow and means capable of detecting the equilibrium of the bridge, said means being connected to a junction between one laminar element and one turbulent element and a junction between the other turbulent element and the other laminar element,
(2) flow regulating means comprising a first pump connected to a supply of fluid from which the fluid is fed into the first bridge, said flow regulating means being controlled by said means capable of detecting equilibrium of the bridge so as to maintain this equilibrium by varying the fluid flow entering the first hydraulic bridge,
(3) a second hydraulic bridge through which the fluid from the first bridge can flow, said second bridge having four identical elements through which the fluid from the first bridge flows turbulently and a constant flow volumetric pump connected to a point between one pair of adjacent elements and a point between the other pair of adjacent elements,

(4) means for measuring the pressure drop across the first hydraulic bridge, and (5) means for measuring the pressure drop across the second bridge.

2. An apparatus according to claim 1 wherein the flow regulating means comprises a constant flow volumetric pump from which a part of the flow is diverted by means of a valve controlled by the first hydraulic bridge equilibrium detector means so as to govern the fluid flow entering the first bridge and maintain the equilibrium of the bridge.

3. An apparatus according to claim 1 wherein the flow regulating means comprises a pump controlled by said means capable of detecting equilibrium of the first hydraulic bridge.

4. An apparatus according to claim 1 which also includes:

(6) an electronic or electric device comprising multipliers and dividers designed for calculating values of viscosities and density and (7) means for displaying or recording these values.

5. An apparatus according to claim 4 wherein the flow regulating means comprises a constant flow volumetric pump from which a part of the flow is diverted by means of a valve controlled by the first hydraulic bridge equilibrium detector means so as to govern the fluid flow entering the first bridge and maintain the equilibrium of the bridge.

6. An apparatus according to claim 4 wherein the flow regulating means comprises a pump controlled by said means capable of detecting equilibrium of the first hydraulic bridge.

* * * * *